(12) United States Patent
Di Fabio et al.

(10) Patent No.: US 7,253,284 B2
(45) Date of Patent: Aug. 7, 2007

(54) CHEMICAL COMPOUNDS

(75) Inventors: Romano Di Fabio, Verona (IT); Fabrizio Micheli, Verona (IT); Yves St-Denis, Verona (IT)

(73) Assignee: Giaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/483,792

(22) PCT Filed: Jul. 15, 2002

(86) PCT No.: PCT/EP02/07865

§ 371 (c)(1),
(2), (4) Date: Jan. 14, 2004

(87) PCT Pub. No.: WO03/008412

PCT Pub. Date: Jan. 30, 2003

(65) Prior Publication Data

US 2004/0171607 A1  Sep. 2, 2004

(51) Int. Cl.
*C07D 471/04* (2006.01)
*A61K 31/437* (2006.01)

(52) U.S. Cl. .................... 546/113; 514/300; 514/232.5
(58) Field of Classification Search .............. 546/113; 544/127; 514/300, 232.5
See application file for complete search history.

(56) References Cited

U.S. PATENT DOCUMENTS

| | | | |
|---|---|---|---|
| 5,006,530 A | 4/1991 | Angerbauer et al. | 514/277 |
| 5,120,782 A | 6/1992 | Hubsch et al. | 514/300 |
| 5,169,857 A | 12/1992 | Angerbauer et al. | 514/344 |
| 5,378,700 A | 1/1995 | Sakuma et al. | 514/212 |
| 5,401,746 A | 3/1995 | Angerbauer et al. | 514/277 |
| 5,502,187 A | 3/1996 | Ayer et al. | 544/117 |
| 5,955,613 A | 9/1999 | Horvath et al. | 546/87 |
| 6,107,301 A | 8/2000 | Aldrich et al. | 514/258 |
| 6,133,282 A | 10/2000 | Horvath et al. | 514/292 |
| 6,355,651 B1 | 3/2002 | Horvath et al. | 514/292 |
| 6,436,932 B1 | 8/2002 | Ge et al. | 514/234.5 |
| 2002/0111490 A1 | 8/2002 | Hovarth et al. | 546/81 |
| 2004/0110785 A1 | 6/2004 | Wang et al. | 514/300 |
| 2004/0167030 A1 | 8/2004 | Bernotas et al. | 504/235 |
| 2004/0176400 A1 | 9/2004 | Capelli et al. | 514/264.11 |
| 2005/0054661 A1 | 3/2005 | De Fabio et al. | 514/265.1 |

FOREIGN PATENT DOCUMENTS

| | | |
|---|---|---|
| DE | 4239440 | 11/1992 |
| EP | 325130 | 1/1989 |
| EP | 415767 | 8/1990 |
| EP | 0 465 970 | 6/1991 |
| EP | 729758 | 2/1996 |
| EP | 773023 | 11/1996 |
| EP | 1040831 | 3/2000 |
| EP | 1103553 | 11/2000 |
| GB | 2248618 | 4/1992 |
| JP | 7010876 | 1/1995 |
| JP | 11335376 A | 12/1999 |
| JP | 2000086663 | 3/2000 |
| WO | WO 91/05784 A | 5/1991 |
| WO | WO 92/12718 | 8/1992 |
| WO | WO 93/20078 | 10/1993 |
| WO | WO 95/10506 | 4/1995 |
| WO | WO 95/33750 | 12/1995 |
| WO | WO 95/34563 | 12/1995 |
| WO | WO 98/05661 | 2/1998 |
| WO | WO 98/08846 | 3/1998 |
| WO | WO 98/08847 | 3/1998 |
| WO | WO 98/35967 | 8/1998 |
| WO | WO 98/45295 | 10/1998 |
| WO | WO 99/07703 | 2/1999 |
| WO | WO 99/51599 | 10/1999 |
| WO | WO 00/58301 | 10/2000 |
| WO | WO 00/58307 | 10/2000 |
| WO | WO 00/58313 | 10/2000 |
| WO | WO 00/66585 | 11/2000 |
| WO | WO 01/23389 | 4/2001 |
| WO | WO 01/53263 | 7/2001 |
| WO | WO 02/02549 | 1/2002 |

(Continued)

OTHER PUBLICATIONS

Chorvat, et al., J. Med. Chem. 1999, 42: 833-848.*

(Continued)

*Primary Examiner*—Rita Desai
(74) *Attorney, Agent, or Firm*—Laura K. Madden; Loretta J. Sauermeich; Mary E. McCarthy

(57) ABSTRACT

Compounds of the formula I,

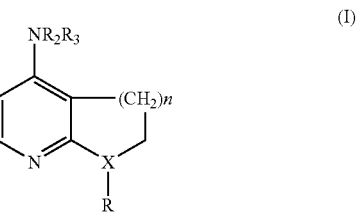

Wherein X is N, n is 1 and R2 and R3 together form a ring, R, R1 and R4 are as defined in the specifications.

1 Claim, No Drawings

FOREIGN PATENT DOCUMENTS

| WO | WO 02/19975 | 3/2002 |
|---|---|---|
| WO | WO 02/055084 | 7/2002 |
| WO | WO 00/58307 | 10/2002 |
| WO | WO 03/022214 | 3/2003 |
| WO | WO 2004/000843 | 12/2003 |
| WO | WO 2004/062665 | 7/2004 |
| WO | WO 2004/094419 | 11/2004 |
| WO | WO 2004/094420 | 11/2004 |

OTHER PUBLICATIONS

He et al., J. Med. Chem. 2000, 43: 449-456.*
Hans Bundgaard, Desing of Produrugs, 1-3 (Elsevier 1985).*
Vippagunta et al., Crystalline Solids, ADV. Drug. Del. Rev., 48:3-26 (2001).*

* cited by examiner

CHEMICAL COMPOUNDS

This application is a 371 of International Application No. PCT/EP02/07865, filed July 15, 2002.

The present invention relates to bicyclic derivatives, to processes for their preparation, to pharmaceutical compositions containing them and to their use in therapy.

The first corticotropin-releasing factor (CRF) was isolated from ovine hypothalami and identified as a 41-amino acid peptide (Vale et al., Science 213: 1394-1397, 1981). CRF has been found to produce profound alterations in endocrine, nervous and immune system function. CRF is believed to be the major physiological regulator of the basal and stress-release of adrenocorticotropic hormone ("ACTH"), Bendorphin and other proopiomelanocortin ("POMC")-derived peptides from the anterior pituitary (Vale et al., Science 213: 1394-1397, 1981).

In addition to its role in stimulating the production of ACTH and POMC, CRF appears to be one of the pivotal central nervous system neurotransmitters and plays a crucial role in integrating the body's overall response to stress.

Administration of CRF directly to the brain elicits behavioral, physiological and endocrine responses identical to those observed for an animal exposed to a stressful environment.

Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224: 889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported.

WO 95/10506 describes inter alia compounds of general formula (A) with general CRF antagonist activity

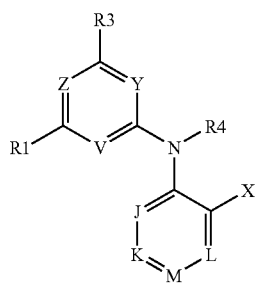

wherein Y may be CR29; V may be nitrogen, Z may be carbon, R3 may correspond to an amine derivative and R4 may be taken together with R29 to form a 5-membered ring and is —CH(R28) when R29 is —CH(R30). There are no specific disclosures of compounds corresponding to this definition.

WO 95/33750 also describes compounds of general formula (B) having CRF antagonistic activity,

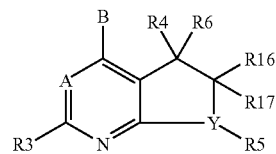

in which A and Y may be nitrogen and carbon and B may correspond to an amine derivative. There are no specific disclosures of compounds corresponding to this definition.

WO 98/08846 describes compounds of general formula (C) having CRF antagonistic activity,

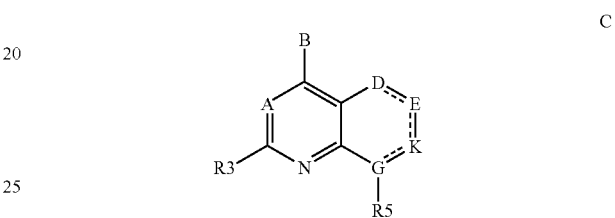

wherein A may be carbon, G may be nitrogen or carbon, B may be an amino derivative and the other groups have the meanings as defined.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

In particular the invention relates to novel compounds which are potent and specific antagonists of corticotropin-releasing factor (CRF) receptors.

The present invention provides compounds of formula (I) including stereoisomers, prodrugs and pharmaceutically acceptable salts or solvates thereof

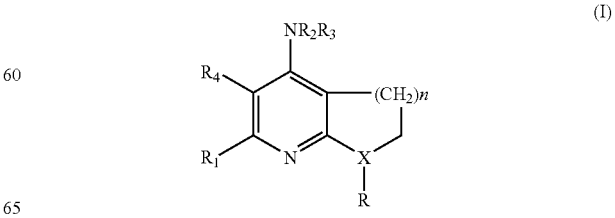

wherein
R is aryl or heteroaryl, each of which may be substituted by 1 to 4 groups selected from:
halogen, C1-C6 alkyl, C1-C6 alkoxy, halo C1-C6 alkyl, C2-C6 alkenyl, C2-C6 alkynyl, halo C1-C6 alkoxy, —C(O)$R_5$, nitro, —$NR_6R_7$, cyano, and a group $R_8$;
$R_1$ is hydrogen, C1-C6 alkyl, C2-C6 alkenyl, C2-C6 alkynyl, halo C1-C6 alkyl, halo C1-C6 alkoxy, halogen, $NR_6R_7$ or cyano;
$R_2$ is hydrogen, C3-C7 cycloalkyl, or a group $R_9$;
$R_3$ is C3-C7 cycloalkyl, or a group $R_9$; or
$R_2$ and $R_3$ together with N form a 5-14 membered heterocycle, which may be substituted by 1 to 3 $R_{10}$ groups;
$R_4$ is hydrogen, C1-C6 alkyl, halogen or halo C1-C6 alkyl;
$R_5$ is a C1-C4 alkyl, —$OR_6$ or —$NR_6R_7$;
$R_6$ is hydrogen or C1-C6 alkyl;
$R_7$ is hydrogen or C1-C6 alkyl;
$R_8$ is a 5-6 membered heterocycle, which may be saturated or may contain one to three double bonds, and which may be substituted by 1 or more $R_{11}$ groups;
$R_9$ is a C1-C6 alkyl that may be substituted by one or more groups selected from: C3-C7 cycloalkyl, C1-C6 alkoxy, haloC1-C6 alkoxy, hydroxy, haloC1-C6 alkyl;
$R_{10}$ is a group $R_8$, C3-C7 cycloalkyl, C1-C6 alkyl, C1-C6 alkoxy, halo C1-C6 alkyl, C2-C6 alkenyl, C2-C6 alkynyl, halo C1-C6 alkoxy, hydroxy, halogen, nitro, cyano, C(O)$NR_6R_7$, phenyl which may be substituted by 1 to 4 $R_{11}$ groups;
$R_{11}$ is C3-C7 cycloalkyl, C1-C6 alkyl, C1-C6 alkoxy, halo C1-C6 alkyl, C2-C6 alkenyl, C2-C6 alkynyl, halo C1-C6 alkoxy, hydroxy, halogen, nitro, cyano, or C(O)$NR_6R_7$;
X is carbon or nitrogen;
n is 1 or 2.

Acid addition salts of the free base amino compounds of the present invention may be prepared by methods well known in the art, and may be formed from organic and inorganic acids. Suitable organic acids include maleic, malic, fumaric, benzoic, ascorbic, succinic, methanesulfonic, p-toluensulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

The solvates may, for example, be hydrates.

References hereinafter to a compound according to the invention include both compounds of formula (I) and their pharmaceutically acceptable acid addition salts together with pharmaceutically acceptable solvates.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as recemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention.

The term C1-C6 alkyl as used herein as a group or a part of the group refers to a linear or branched alkyl group containing from 1 to 6 carbon atoms; examples of such groups include methyl, ethyl, propyl, isopropyl, n-butyl, isobutyl, tert butyl, pentyl or hexyl.

The term C3-C7 cycloalkyl group means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term halogen refers to a fluorine, chlorine, bromine or iodine atom.

The term halo C1-C6 alkyl, or halo C1-C2 alkyl means an alkyl group having one or more carbon atoms and wherein at least one hydrogen atom is replaced with halogen such as for example a trifluoromethyl group and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a linear or a branched chain alkoxy group, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as $OCHF_2$, or $OCF_3$.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term aryl means an aromatic carbocyclic moiety such as phenyl, biphenyl or naphthyl.

The term heteroaryl means an aromatic heterocycle ring of 5 to 10 members and having at least one heteroatom selected from nitrogen, oxygen and sulfur, and containing at least 1 carbon atom, including both mono-and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, triazolyl, tetrazolyl, and quinazolinyl.

The term 5-14 membered heterocycle means a 5 to 7-membered monocyclic, or 7-to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term 5-6 membered heterocycle means, according to the above definition, a 5-6 monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles include heteroaryls as defined above. The heterocycle may be attached via any heteroatom or carbon atom. Thus, the term include (but are not limited to) morpholinyl, pyridinyl, pyrazinyl, pyrazolyl, thiazolyl, triazolyl, imidazolyl, oxadiazolyl, oxazolyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

Representative compounds of this invention include the following structure (Ia) and (Ib)

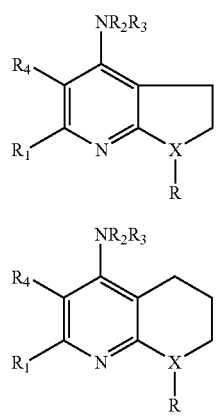

In one preferred embodiment in which n is 1, according to the definition of the compounds of formula (I) above, the CRF receptor antagonists of this invention have structure (Ia), and, when n is 2, then the CRF receptor antagonists of this invention have structure (Ib), wherein R, $R_1$, $R_2$ and $R_3$ are defined as above.

Further representative compounds of this invention include compounds of general formula (I) in which
$R_2$ and $R_3$ together with N form a 5-14 membered heterocyclic group, which may be substituted by 1 to 3 $R_{10}$ groups; such $R_{10}$ groups are defined as above.

Depending upon the choice of X, the CRF receptor antagonists of this invention include compounds of formula (IIa) and (IIb), in which the group $NR_2R_3$ represents a 5-6 membered heterocyclic group, which may be substituted by 1 to 3 $R_8$ groups.

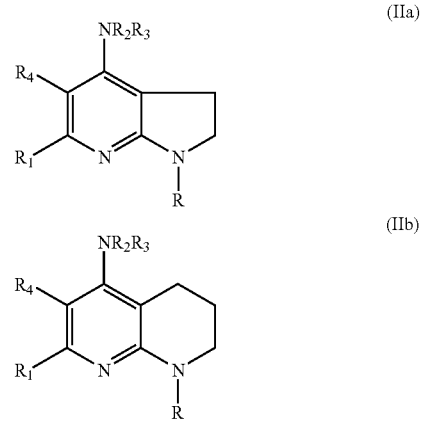

In particular compounds of formula (IIIa) and (IIIb) are included

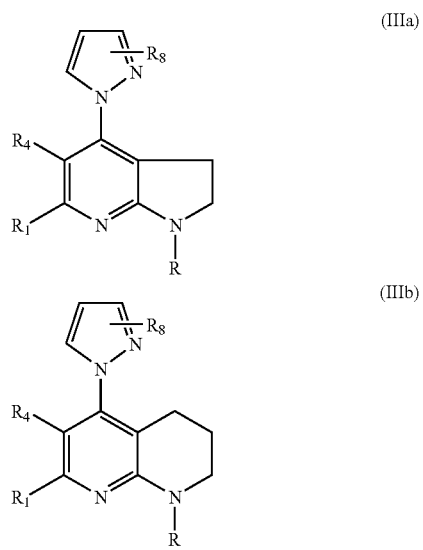

in which $R_1$, R and $R_8$ have the meanings as defined before.

Examples of such compounds are reported in the Experimental Part.

Even more preferred embodiments of the invention include, but are not limited to, compounds of the formula (I), (Ia), (Ib), (IIa), (IIb), (IIIa), (IIIb):

wherein:
  $R_1$ is C1-C3 alkyl group or halo C1-C3 alkyl group, preferably methyl or trifluoromethyl;
  $R_4$ is hydrogen; and
  R is an aryl group selected from: 2,4-dichlorophenyl, 2-chloro-4-methylphenyl, 2-chloro-4-trifluoromethyl, 2-chloro-4-methoxyphenyl, 2,4,5-trimethylphenyl, 2,4-dimethylphenyl, 2-methyl-4-methoxyphenyl, 2-methyl-4-chlorophenyl, 2-methyl-4-trifluoromethyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 2-methyl-4-cyanophenyl, 2-chloro-4-cyanophenyl, 4-methyl-6-dimethylaminopyridin-3-yl, 3,5-dichloro-pyridin-2-yl, 2,6-bismethoxy-pyridin-3-yl and 3-chloro-5-trichloromethyl-pyridin-2-yl.

Preferred compounds according to the invention are:
1-(2,4-bis-trifluoromethyl-phenyl)-6-methyl-4-(3-thiazol-2-yl-pyrazol-1-yl)-2,3-dihydro-1H-pyrrolo[2,3-b]pyridine;
1-(2,4-bis-trifluoromethyl-phenyl)-6-methyl-4-(3-thiazol-2-yl-pyrazol-1-yl)-2,3-dihydro-1H-pyrrolo[2,3-b]pyridine;
3-methyl-4-[6-methyl-4-(3-thiazol-2-yl-pyrazol-1-yl)-2,3-dihydro-1H-pyrrolo[2,3-b]pyridin-1-yl]-benzonitrile;
4-[6-methyl-4-(3-thiazol-2-yl-pyrazol-1-yl)-2,3-dihydro-1H-pyrrolo[2,3-b]pyridin-1-yl]-3-trifluoromethyl-benzonitrile;
6-methyl-1-(2-methyl-4-trifluoromethoxy-phenyl)-4-(3-thiazol-2-yl-pyrazol-1-yl)-2,3-dihydro-1H-pyrrolo[2,3-b]pyridine;
1-(2,4-bis-trifluoromethyl-phenyl)-7-methyl-5-(3-thiazol-2-yl-pyrazol-1-yl)-1,2,3,4-tetrahydro-[1,8]naphthyridine;
1-(4-methoxy-2-methyl-phenyl)-6-methyl-4-(3-thiazol-2-yl-pyrazol-1-yl)-2,3-dihydro-1H-pyrrolo[2,3-b]pyridine
1-(2,4-bis-trifluoromethyl-phenyl)-6-methyl-4-(3-morpholin-4-yl-pyrazol-1-yl)-2,3-dihydro-1H-pyrrolo[2,3-b]pyridine
1-(2,4-bis-trifluoromethyl-phenyl)-6-methyl-4-(3-pyridin-2-yl-pyrazol-1-yl)-2,3-dihydro-1H-pyrrolo[2,3-b]pyridine
4-[1,3']bipyrazolyl-1'-yl-1-(2,4-bis-trifluoromethyl-phenyl)-6-methyl-2,3-dihydro-1H-pyrrolo[2,3-b]pyridine.

In general, the compounds of structure (I) may be made according to the organic synthesis techniques known to those skilled in this field, as well as by the representative methods set forth in the Examples.

Compounds of formula (I), and salts and solvates thereof, may be prepared by the general methods outlined hereinafter. In the following description, the groups R, $R_1$, $R_2$, $R_3$, $R_4$, $R_5$, $R_6$, $R_7$, $R_8$, $R_9$, $R_{10}$, $R_{11}$, and n have the meanings as previously defined for compounds of formula (I) unless otherwise stated.

Compounds of formula (IIa) may be conveniently prepared according to the following Scheme 1:

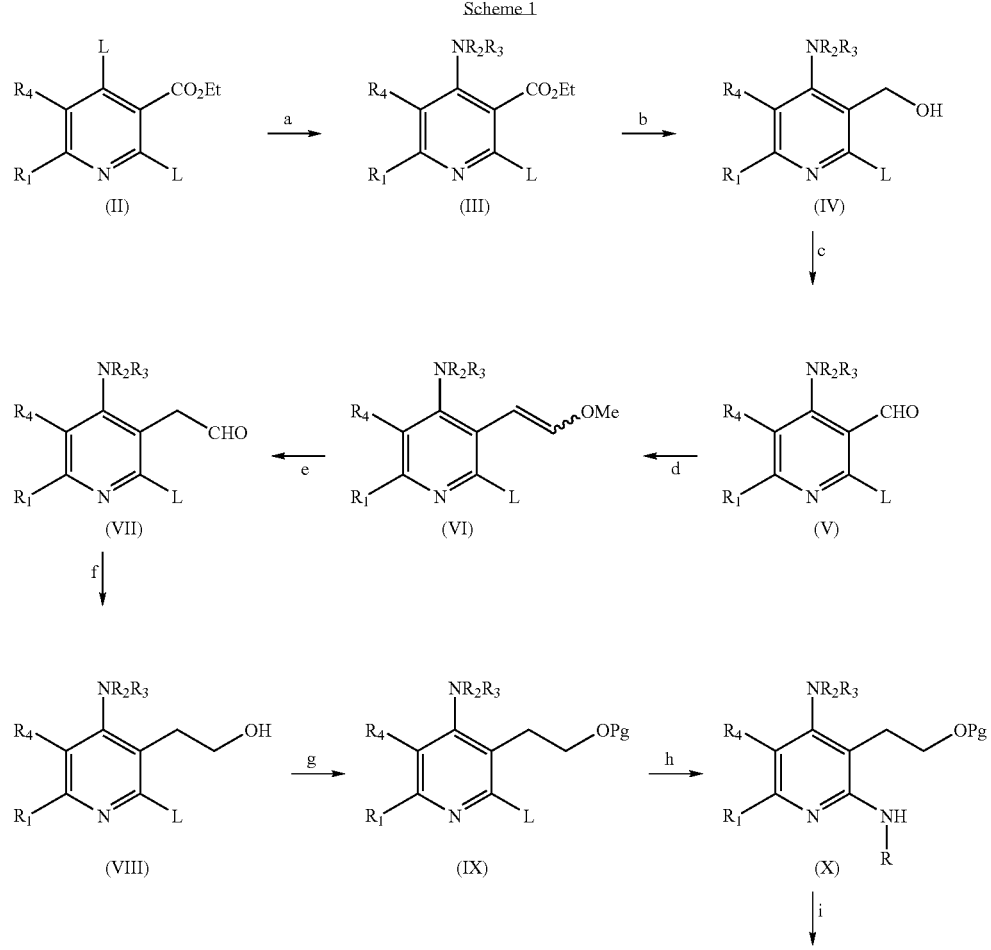

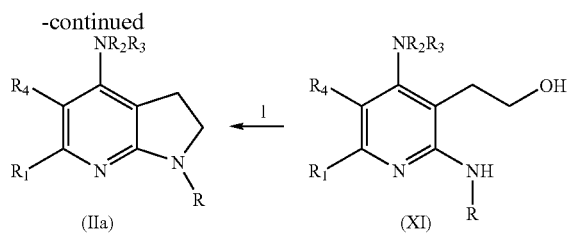

in which step a stands for conversion of the leaving group L, selected in a group consisting from: halogen or reactive residue of sulphonic acid (e.g. mesylate, tosylate), preferably chloride, in the amino group of compounds (III), by reaction with the suitable amine $NR_2R_3$ in basic conditions;

step 1 stands for intramolecular cyclisation by heating after conversion of the hydroxy group of compounds (XI) in a suitable leaving group (such as bromide, by reaction with $CBr_4$ and $PPh_3$) to give the final compounds (IIa).

Alternatively, compounds of formula (IIa) may be conveniently prepared according to the following Scheme 2:

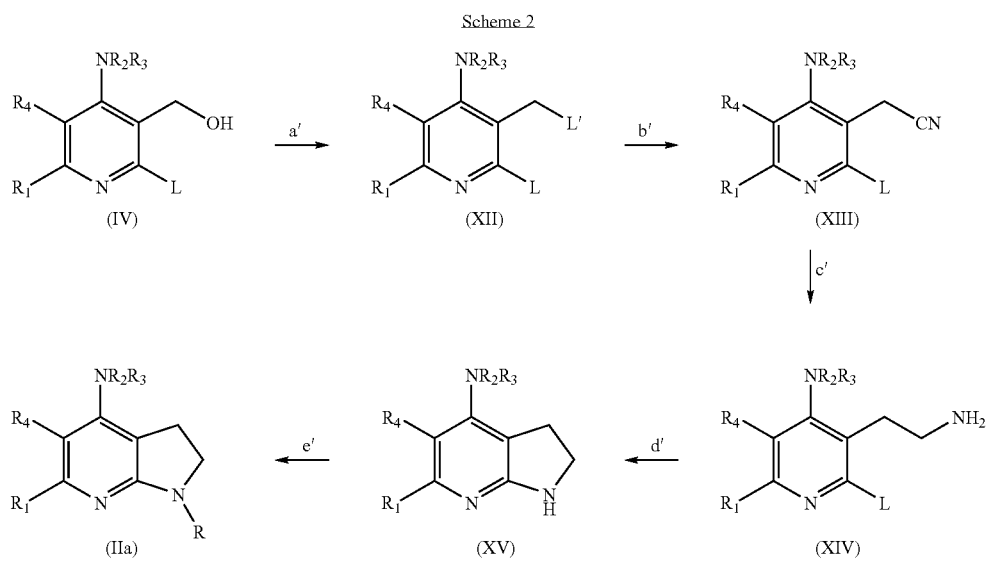

step b stands for reduction of the ester group with a suitable reducing agent (such as DIBAl—H) to hydroxy group of compounds (IV);

step c stands for oxidation of the hydroxy group with a suitable oxidising agent (such as Dess-Martin periodinane) to aldehyde group of compound (V);

step d stands for formation of the aldehyde group of compounds (VII) by Wittig reaction in the usual conditions, through formation of enol ether followed by acid hydrolysis (step e);

step f stands for reduction of the aldehyde group with a suitable reducing agent (such as $NaBH_4$) to hydroxy group of compounds (VIII);

step g stands for conversion of the hydroxy group in the suitable protecting group of compounds (IX)(such as TBS: tert-butyldimethylsilyl);

step h stands for Buchwald reaction by coupling with the suitable amine $RNH_2$;

step i stands for deprotection reaction to give the hydroxy group of compounds (XI);

in which step a' stands for conversion of the hydroxy group in a suitable leaving group L' of compounds (XII), which, independently from L, has the same definition (e.g mesylate, by reaction with MsCl in $Et_3N$);

step b' stands for conversion of L' in the cyano derivative of compounds (XIII) by reaction with, e.g. KCN in an aprotic dipolar solvent, like DMF;

step c' stands for reduction of the cyano group with a suitable reducing agent agent (such as $BH_3$-THF) to the amino group of compound (XIV);

step d' stands for intramolecular cyclisation of compounds (XIV) by heating in a suitable solvent (such as NMP) at high temperature;

step e' stands for reduction of the aldehyde group with a suitable reducing agent (such as $NaBH_4$) to hydroxy group of compounds (VIII);

step f' corresponds to previous step h.

Compounds of formula (IIb) may be conveniently prepared according to the following Scheme 3:

Scheme 3

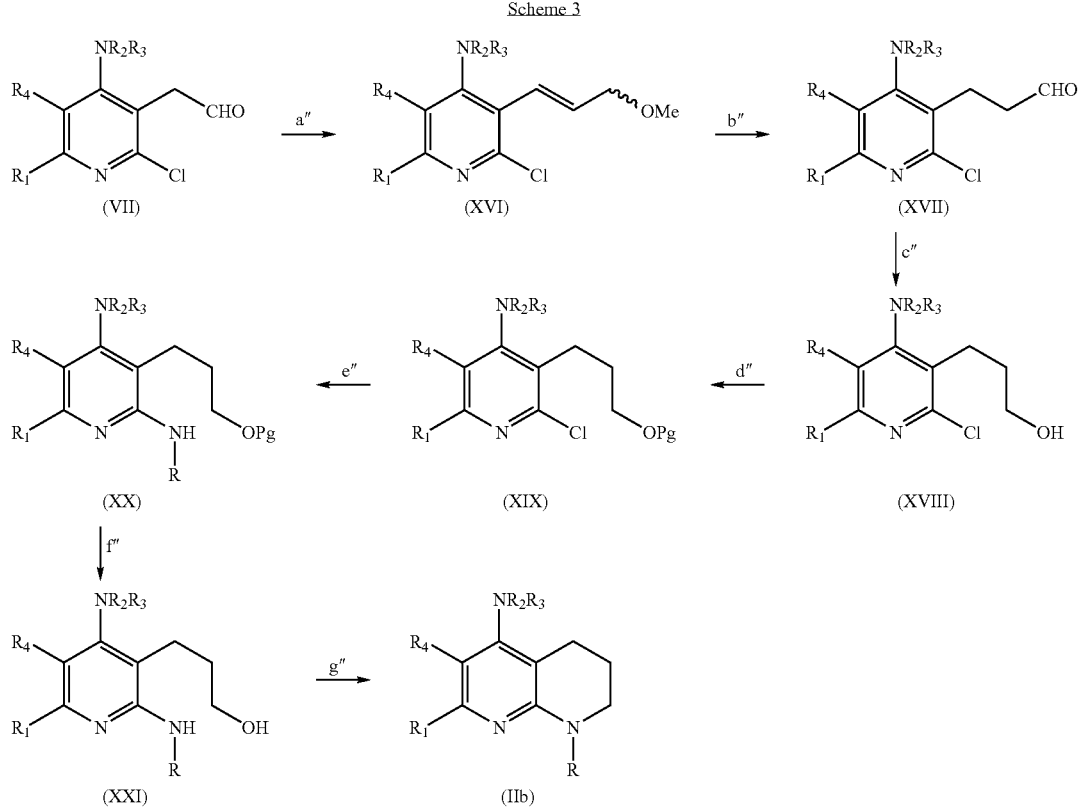

in which:
step a" corresponds to previous step d;
step b" corresponds to previous step e;
step c" corresponds to previous step f;
step d" corresponds to previous step g;
step e" corresponds to previous step h;
step f" corresponds to previous step i;
step g" corresponds to previous step l;

Compounds of formula (II) are known compounds or may be prepared according to known methods in the literature.

Compounds of formula (IIIa) and (IIIb) may be prepared according to the previous Schemes 1, 2 and 3, once prepared the heterocyclic reactive residue according to known methods to the skilled in the art.

Examples of suitable hydroxy protecting group include trihydrocarbyl silyl ethers such as the trimethylsilyl or t-butyldimethylsilyl ether. The hydroxyl protecting groups may be removed by well-known standard procedures (such as those described in Protective Groups in Organic Chemistry, pages 46-119, Edited by J F W McOmie (Plenum Press, 1973)). For example when Pg is a t-butyldimethylsilyl group, this may be removed by treatment with triethylamine trihydrofluoride.

Pharmaceutical acceptable salts may also be prepared from other salts, including other pharmaceutically acceptable salts, of the compound of formula (I) using conventional methods.

The compounds of formula (I) may readily be isolated in association with solvent molecules by crystallisation or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The CRF receptor antagonists of the present invention demonstrate activity at the CRF receptor site including CRF 1 and CRF 2 receptors and may be used in the treatment of conditions mediated by CRF or CRF receptors.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7: 88, 1987) and Battaglia et al. (Synapse 1: 572, 1987).

The CRF receptors-binding assay was performed by using the homogeneous technique of scintillation proximity (SPA). The ligand binds to recombinant membrane preparation expressing the CRF receptors which in turn bind to wheatgerm agglutinin coated SPA beads. In the Experimental Part will be disclosed the details of the experiments.

With reference to CRF receptor binding affinities, CRF receptor antagonists of this invention have a Ki less than 10 μm.

Compounds of the invention are useful in the treatment of central nervous system disorders where CRF receptors are involved. In particular in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganised schizophrenia, catatonic schizophrenia, undifferentiated schizophrenia, residual schizoprenia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa and bulimia.

Compounds of the invention are also useful in the treatment of sleep disorders including dysomnia, insomnia, sleep apnea, narcolepsy, and circadian ritmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome (IBS); skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by CRF.

In an alternative or further aspect there is provided a method for the treatment of a mammal, including man, in particular in the treatment of condition mediated by CRF, comprising administration of an effective amount of a compound of formula (I) or a pharmaceutically acceptable salt or a solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

EXAMPLES

In the Intermediates and Examples unless otherwise stated:

Melting points (m.p.) were determined on a Gallenkamp m.p. apparatus and are uncorrected. All temperatures refers to ° C. Infrared spectra were measured on a FT-IR instrument. Proton Magnetic Resonance ($^1$H-NMR) spectra were recorded at 400 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromathography was carried out over silica gel (Merck AG Darmstaadt, Germany). The following abbreviations are used in text: EtOAc=ethyl acetate, cHex=cyclohexane, CH$_2$Cl$_2$=dichloromethane, Et$_2$O=dietyl ether, DMF=N,N'-dimethylformamide, DIPEA=N,N-diisopropylethylamine, DME=ethylene glycol dimethyl ether, MeOH=methanol, Et$_3$N=triethylamine, TFA=trifluoroacetic acid, THF=tetrahydrofuran, DIBAL-H=diisobutylaluminium hydride, DMAP=dimethylaminopyridine, LHMDS=lithiumhexamethyldisilazane; Tlc refers to thin layer chromatography on silica plates, and dried refers to a solution dried over anhydrous sodium sulphate; r.t. (RT) refers to room temperature.

Intermediate 1

2,4-Dichloro-6-methyl-nicotinic acid ethyl ester

The title compound was prepared according to an already published procedure: Mittelbach, Martin; *Synthesis*, 1988, 6, p. 479-80.

Intermediate 2

2-Chloro-6-methyl-4-(3-thiazol-2-yl-pyrazol-1-yl)-nicotinic acid ethyl ester

To a solution of 2-(1H-pyrazol-3-yl)-1,3-thiazole (7.71 g, 1.05 eq) in anh. DMF (61 mL), at 0° C., under N$_2$, was added NaH 60% in mineral oil (2.03 g, 1.05 eq) and the reaction mixture was stirred for 10 min. at 0° C. and then for 1 hr at room temperature. Intermediate 1 (11.34 g, 48.0 mmol) was then added as a solution in anh. DMF (35 mL) at 0° C. and the resulting solution was heated at 110° C. for 3 hr. The reaction was then quenched with water, extracted with EtOAc, washed with brine, dried over anh. Na$_2$SO$_4$, filtered and concentrated in vacuo. The crude product was purified by flash chromatography (silica gel, cHex/EtOAc 7:3) to give 7.02 g of the title compound as a white solid.

NMR ($^1$H, CDCl$_3$): δ 7.91 (d, 1H), 7.91 (d, 1H), 7.41 (d, 1H), 7.31 (s, 1H), 7.18 (d, 1H), 4.50 (q, 2H), 2.78 (s, 3H), 1.25 (t, 3H). MS (m/z): 349 [MH]$^+$.

Intermediate 3

[2-Chloro-6-methyl-4-(3-thiazol-2-yl-pyrazol-1-yl)-pyridin-3-yl]-methanol

To a solution of intermediate 2 (1.5 g, 4.3 mmol) in anh. CH$_2$Cl$_2$ (30 mL), at −78° C., under N$_2$, was added DIBAl—H 1.0 M in cyclohexane (12.9 mL, 3.0 eq). The reaction mixture was stirred for 1 hr at −78° C. and then for 1 hr at room temperature. The reaction was then quenched with a saturated solution of Rochelle's salt, extracted with EtOAc, washed with brine, dried over anh. Na$_2$SO$_4$, filtered and concentrated in vacuo. The crude product was purified by flash chromatography (silica gel, cHex/EtOAc 1:1) to give 1.02 g of the title compound as a white solid.

NMR ($^1$H, CDCl$_3$): δ 8.05 (d, 1H), 7.90 (d, 1H), 7.40 (d, 1H), 7.25 (s, 1H), 7.10 (d, 1H), 4.65 (S, 2H), 4.0 (bs, 1H), 2.60 (s, 3H). MS (m/z): 307 [M]$^+$.

Intermediate 4

2-Chloro-6-methyl-4-(3-thiazol-2-yl-pyrazol-1-yl)-pyridine-3-carbaldehyde

To a solution of intermediate 3 (150 mg, 0.5 mmol) in anh. CH$_2$Cl$_2$ (5 mL), at room temperature, under N$_2$, was added the Dess Martin periodinane (237 mg, 1.12 eq) and the reaction mixture was stirred for 1 hr at room temperature. The reaction was then quenched with a solution of 0.5 g of sodium thiosulfate dissolved in a saturated solution of sodium bicarbonate, extracted with EtOAc, washed with brine, dried over Na$_2$SO$_4$, filtered and concentrated in vacuo. The crude product was purified by flash chromatography (silica gel, cHex/EtOAc 1:1) to give 124 mg of the title compound as a white solid.

NMR ($^1$H, CDCl$_3$): δ 10.4 (s, 1H), 8.0-7.9 (2d, 2H), 7.40 (2d, 2H), 7.10 (s, 1H), 2.70 (s, 3H). MS (m/z): 305 [MH]$^+$.

Intermediate 5

2-Chloro-3-(2-methoxy-vinyl)-6-methyl-4-(3-thiazol-2-yl-pyrazol-1-yl)-pyridine

To a solution of (methoxymethyl)-triphenylphosphonium chloride (4.24 g, 3 eq) in anh. THF (20 mL), at 0° C., under N$_2$, was added n-BuLi 1.6 M in cyclohexane (7.73 ml, 12.37 mmol) and the reaction mixture was brought to room temperature and then stirred for 15 min. A solution of intermediate 4 (1.25 g, 4.1 mmol) in anh. THF (15 mL) was then added and the reaction was stirred at room temperature for 1.5 hr. The reaction was then quenched with water, extracted with EtOAc, washed with brine, dried over anh. Na$_2$SO$_4$, filtered and concentrated in vacuo. The crude product was purified by flash chromatography (silica gel, cHex/EtOAc 4:1) to give 961 mg of the title compound as a white solid (E:Z=3:2 mixture, used as such in the next step).

NMR ($^1$H, CDCl$_3$) principal E product: δ 7.90 (m, 1H), 7.83 (m, 1H), 7.38 (m, 1H), 7.05 (m, 1H), 7.00 (m, 1H), 6.51 (d, 1H), 5.63 (d, 1H), 3.64 (s, 3H), 2.60 (s, 3H). MS (m/z): 333 [MH]$^+$.

Intermediate 6

[2-Chloro-6-methyl-4-(3-thiazol-2-yl-pyrazol-1-yl)-pyridin-3-yl]-acetaldehyde

To a solution of intermediate 5 (936 mg, 2.8 mmol) in anh. THF (15 mL) was added 6N HCl (21 ml, 45 eq) and the reaction mixture was stirred at room temperature for 15 hr. The reaction was then quenched with sat. aq. NaHCO$_3$ until pH=7, extracted with EtOAc, washed with brine, dried over anh. Na$_2$SO$_4$, filtered and concentrated in vacuo to give 893 mg of the title compound as a white solid, which was used in the next step without further purification.

NMR ($^1$H, CDCl$_3$): δ 9.80 (s, 1H), 7.90-7.80 (2d, 2H), 7.70 (d, 1H), 7.20 (d, 1H), 7.0 (s, 1H), 4.25 (s, 2H), 2.70 (s, 3H). MS (m/z): 319 [MH]$^+$.

Intermediate 7

2-[2-Chloro-6-methyl-4-(3-thiazol-2-yl-pyrazol-1-yl)-pyridin-3-yl]-ethanol

To a solution of intermediate 6 (903 mg, 2.84 mmol) in anh. MeOH (10 mL) were added CeCl$_3$ (700 mg, 1 eq) and NaBH$_4$ (107 mg, 1 eq) and the reaction mixture was stirred at room temperature for 5 min. The reaction was then quenched with water, extracted with ethyl acetate, washed with brine, dried over anh. Na$_2$SO$_4$, filtered and concentrated in vacuo to give 848 mg of the title compound as a white solid, which was used in the next step without further purification.

NMR ($^1$H, CDCl$_3$): δ 8.00 (m, 2H), 7.50 (d, 1H), 7.20 (m, 2H), 4.25 (t, 2H), 3.20 (t, 2H), 2.70 (s, 3H). MS (m/z): 321 [MH]$^+$.

Intermediate 8

3-[2-(tert-Butyl-dimethyl-silanyloxy)-ethyl]-2-chloro-6-methyl-4-(3-thiazol-2yl-pyrazol-1-yl)-pyridine To a solution of intermediate 7 (840 mg, 2.6 mmol) in anh. CH$_2$Cl$_2$ (10 mL) were added 2,6-lutidine (0.67 ml, 2.2 eq) and tert-butyldimethylsilyl triflate (0.89 ml, 1.5 eq) and the reaction mixture was stirred at room temperature for 15 hr. The reaction was then quenched with an aqueous solution of saturated NH$_4$Cl, extracted with EtOAc, washed with brine, dried over anh. Na$_2$SO$_4$, filtered and concentrated in vacuo. The product was purified by flash chromatography (silica gel, cHex/EtOAc 3:2) to give 950 mg of the title compound as a colorless oil.

NMR ($^1$H, CDCl$_3$): δ 8.20 (d, 1H), 7.75 (d, 1H), 7.35 (d, 1H), 7.00 (m, 2H), 4.00 (t, 2H), 3.05 (t, 2H), 2.55 (s, 3H), 0.80 (s, 9H), −0.10 (s, 6H). MS (m/z): 435 [MH]$^+$.

Intermediate 9

(2,4-Bis-trifluoromethyl-phenyl)-[3-[2-(tert-butyl-dimethyl-silanyloxy)-ethyl]-6-methyl-4-(3-thiazol-2-yl-pyrazol-1-yl)-pyridin-2-yl]-amine To a solution of intermediate 8 (240 mg, 0.553 mmol) in anh. DME (1 mL) were added Pd$_2$(dba)$_3$ (51 mg, 0.1 eq), 2-(dicyclohexylphosphino)-2'-methylbiphenyl (60 mg, 0.3 eq), K$_3$PO$_4$ (317 mg, 3 eq) and 2,4-bis(trifluoromethyl) aniline (0.17 ml, 2 eq) and the reaction mixture was submitted to microwave irradiation (150 W, 100° C., 60 psi) for 20 min. The reaction was then quenched with an aqueous solution of saturated NH$_4$Cl, extracted with EtOAc, washed with brine, dried over anh. Na$_2$SO$_4$, filtered and concentrated in vacuo. The product was purified by flash chromatography (silica gel, cHex/EtOAc 9:1) to give 180 mg of the title compound as a colorless oil.

NMR ($^1$H, CDCl$_3$): δ 8.55 (d, 1H), 8.20 (bs, 1H), 7.90 (d, 1H), 7.80 (m, 2H), 7.65 (dd, 1H), 7.40 (d, 1H), 7.05 (d, 1H), 6.85 (s, 1H), 4.20 (t, 2H), 2.90 (t, 2H), 2.60 (s, 3H), 0.80 (s, 9H), 0.10 (s, 6H). MS (m/z): 628 [MH]$^+$.

Intermediate 10

2-[2-(2,4-Bis-trifluoromethyl-phenylamino)-6-methyl-4-(3-thiazol-2-yl-pyrazol-1-yl)pyridin-3-yl]-ethanol To a solution of intermediate 9 (240 mg, 0.38 mmol) in anh. THF (5 mL) was added Et$_3$N.3HF (0.187 ml, 3 eq) and the reaction mixture was stirred for 15 hr at room temperature. The reaction was then quenched with an aqueous solution of saturated NH$_4$Cl, extracted with EtOAc, washed with brine, dried over anh. Na$_2$SO$_4$, filtered and concentrated in vacuo. The product was purified by flash chromatography (silica gel, cHex/EtOAc 1:1) to give 180 mg of the title compound as a colorless oil.

NMR ($^1$H, CDCl$_3$): δ 8.45 (bs, 1H), 8.20 (d, 1H), 7.85 (d, 1H), 7.85 (2d, 2H), 7.65 (dd, 1H), 7.30 (d, 1H), 7.05 (d, 1H), 6.85 (s, 1H), 4.20 (t, 2H), 2.85 (t, 2H), 2.50 (s, 3H). MS (m/z): 514 [MH]$^+$.

Intermediate 11

Methanesulfonic acid 2-chloro-6-methyl-4-(3-thiazol-2-yl-pyrazol-1-yl)-pyridin-3-ylmethyl ester To a solution of intermediate 3 (308 mg, 1.01 mmol) in anh. CH$_2$Cl$_2$ (2.5 mL), at −25° C., under N$_2$, was added Et$_3$N (280 µL, 2 eq) and CH$_3$SO$_2$Cl (120 µL, 1.5 eq). The reaction mixture was stirred at −25° C. for 2 hr and than at −5° C. for another 2 hr. The reaction mixture was diluted with water and extracted with CH$_2$Cl$_2$. The combined organic extracts were dried over anh. Na$_2$SO$_4$, filtered and concentrated in vacuo. The crude product was purified by flash chromatography (silica gel, cHex/EtOAc 6:4→1:1) to give 88 mg of the title compound as a colourless oil.

NMR ($^1$H, CDCl$_3$): δ 7.90 (d, 1H), 7.87 (d, 1H), 7.39 (d, 1H), 7.34 (s, 1H), 7.14 (d, 1H), 5.5 (s, 2H), 3.0 (s, 3H), 2.78 (s, 3H). MS (m/z): 385 [MH]$^+$, Cl

Intermediate 12

[2-Chloro-6-methyl-4-(3-thiazol-2-yl-pyrazol-1-yl)-pyridin-3-yl]-acetonitrile

To a solution of intermediate 11 (88 mg, 0.229 mmol) in anh. DMF (2.5 mL), at 0° C., under N$_2$, was added KCN (15 mg, 1 eq). The reaction mixture was stirred at room temperature for 5 hr. The reaction mixture was diluted with water and 1M NaOH and extracted with Et$_2$O. The combined organic extracts were dried over anh. Na$_2$SO$_4$, filtered and concentrated in vacuo. The title compound was obtained as a yellow solid (60 mg) and was used in the next step without further purification.

NMR ($^1$H, CDCl$_3$): δ 7.92 (d, 1H), 7.91 (d, 1H), 7.41 (d, 1H), 7.31 (s, 1H), 7.18 (d, 1H), 3.99 (s, 2H), 2.78 (s, 3H). MS (m/z): 316 [MH]$^+$, Cl

Intermediate 13

2-[2-Chloro-6-methyl-4-(3-thiazol-2-yl-pyrazol-1-yl)-pyridin-3-yl]-ethylamine

To a solution of intermediate 12 (810 mg, 2.571 mmol) in anh. THF (6 mL), at r.t., under N$_2$, was added BH$_3$.THF (10.3 mL, 4 eq). The reaction mixture was stirred at reflux temperature for 2 hr. The reaction mixture was concentrated in vacuo and diluted with MeOH. 1M HCl in Et$_2$O (7.7 μL, 3 eq) was added at r.t. and the solution was stirred at reflux for 2 hr. The reaction mixture was diluted with water and basified with 1M NaOH to pH=12. The crude product was purified by flash chromatography (silica gel CH$_2$Cl$_2$/MeOH 6:4). The title compound was obtained as a pale yellow solid (690 mg).

NMR ($^1$H, CDCl$_3$): δ 8.42 (d, 1H), 7.94 (d, 1H), 7.79 (d, 1H), 7.48 (s, 1H), 7.07(d, 1H), 2.81 (m, 4H), 2.51 (s, 3H), 2.0 (bs, 2H). MS (m/z): 320 [MH]$^+$, Cl

Intermediate 14

6-Methyl-4-(3-thiazol-2-yl-pyrazol-1-yl)-2,3-dihydro-1H-pyrrolo[2,3-b]pyridine

To a solution of intermediate 13 (640 mg, 2.01 mmol) in dry N-methylpyrrolidinone (13 mL), at r.t., under N$_2$, was added Et$_3$N (1.12 mL, 4 eq). The reaction mixture was stirred at 110° C. for 7 hr. The reaction mixture was diluted with water and extracted with EtOAc. The combined organic extracts were dried over anh. Na$_2$SO$_4$, filtered and concentrated in vacuo. The crude product was purified by flash chromatography (silica gel, CH$_2$Cl$_2$/MeOH 98:2). The title compound was obtained as white solid (187 mg).

NMR ($^1$H, CDCl$_3$): δ 7.98 (d, 1H), 7.89 (d, 1H), 7.35 (d, 1H), 7.06 (d, 1H), 4.65 (bs, 1H), 3.72 (t, 2H), 3.48 (t, 2H), 2.42 (s, 3H) MS (m/z): 284 [MH]$^+$

Intermediate 15

2-Chloro-3-(3-methoxy-allyl)-6-methyl-4-(3-thiazol-2-yl-pyrazol-1-yl)-pyridine

To a stirred suspension of (methoxy-methyl) triphenylphosphonium chloride (833 mg, 3 eq.) in anh. THF (4 mL) was added dropwise, at 0° C., under N$_2$, n-BuLi in hexanes 1.6 M (1.50 ml, 3 eq). The reaction mixture was stirred at r.t. for 15 min before a solution of intermediate 6 (258 mg, 1 eq) in anh. THF (3 ml) was added. The reaction mixture was stirred for 1.5 hr. The mixture was quenched with water and extracted with EtOAc. The combined organic extracts were dried over anh. Na$_2$SO$_4$, filtered and concentrated to dryness in vacuo. The crude product was purified by flash chromatography (silica gel, cHex/EtOAc 8:2) to give 220 mg of the title compound as an unseparable mixture of trans and cis (60/40) vinyl ether (yellow oil, 78%)

NMR ($^1$H, CDCl$_3$): δ 7.88 (d, 1H), 7.79 (d, 1H), 7.36 (d, 1H), 7.19 (s, 1H), 7.08 (d, 1H), 6.31 (d, 1H), 4.90 (m, 1H), 3.44 (d, 2H), 3.48 (s, 3H), 2.57 (s, 3H). MS (m/z): 347 [MH]$^+$, 1 Cl

Intermediate 16

3-[2-Chloro-6-methyl-4-(3-thiazol-2-yl-pyrazol-1-yl)-pyridin-3-yl]-propionaldehyde To a solution of intermediate 15 (370 mg, 1.07 mmol) in THF (5 mL) was added HCl 6 N (12 ml, 67.5 eq) and the reaction mixture was stirred for 13 hr at r.t. A solution of NaHCO$_3$ was added to the reaction mixture until pH=7 was reached and the aqueous phase was extracted with EtOAc. The combined organic extracts were dried over anh. Na$_2$SO$_4$, filtered and concentrated to dryness in vacuo. The crude title compound (335 mg) was used in the following step without further purification.

NMR ($^1$H, CDCl$_3$): δ 9.84 (s, 1H), 7.84 (d, 1H), 7.75 (d, 1H), 7.30 (d, 1H), 7.06 (d, 1H), 7.05 (s, 1H), 3.10-3.30 (m, 4 H), 2.55 (s, 3H). MS (m/z): 333 [M+1]$^+$, 1Cl

Intermediate 17

3-[2-Chloro-6-methyl-4-(3-thiazol-2-yl-pyrazol-1-yl)-pyridin-3-yl]-propan-1-ol

To a solution of intermediate 16 (335 mg, 1 mmol) in anh. CH$_3$OH (5 mL) were added CeCl$_3$ (247 mg, 1 eq) and NaBH$_4$ (38 mg, 1 eq) at r.t., under N$_2$. The reaction mixture was stirred for 20 min. The solvent was removed in vacuo and the residue was redissolved in EtOAc/H$_2$O and the layers were separated. The aqueous layer was extracted with EtOAc, and the combined organic extracts were dried over anh. Na$_2$SO$_4$, filtered, and concentrated in vacuo. Purification (silica gel, cHex/EtOAc 8:2) of the crude afforded 277.4 mg of the title compound as a clear oil.

NMR ($^1$H, CDCl$_3$): δ 7.90 (d, 1H), 7.76 (d, 1H), 7.36 (d, 1H), 7.12 (s, 1H), 7.07 (d, 1H), 3.70 (m, 2H), 2.90 (t, 2H), 2.58 (s, 3H), 2.20 (bt, 1H), 2.04 (m, 2H). MS (m/z): 335 [M+1]$^+$, 1Cl

Intermediate 18

3-[3-(tert-Butyl-dimethyl-silanyloxy)-propyl]-2-chloro-6-methyl-4-(3-thiazol-2-yl-pyrazol-1-yl)-pyridine To a solution of intermediate 17 (277.4 mg, 0.83 mmol) in anh. DMF (7 mL) was added imidazole (621 mg, 11 eq), tert-butyldimethylsilyl chloride (350 mg, 2.8 eq) and a catalytic amount of DMAP at 0° C. under N$_2$. The reaction mixture was stirred at room temperature for 2 hr. Then a saturated aqueous solution of NH$_4$Cl was added to the reaction mixture and it was extracted with EtOAc. The combined organic extracts were dried over anh. Na$_2$SO$_4$, filtered and concentrated in vacuo. The crude product was purified by flash chromatography (silica gel, cHex/EtOAc 7:3) to give 347 mg of the title compound as a yellow oil.

NMR ($^1$H, CDCl$_3$): δ 7.89 (d, 1H), 7.81 (d, 1H), 7.34 (d, 1H), 7.20 (s, 1H), 7.08 (d, 1H), 3.66 (t, 2H), 2.86 (m, 2H), 2.57 (s, 3H), 1.89 (m, 2H), 0.86 (s, 9H), −0.006 (s, 6H). MS (m/z): 449 [M]$^+$, 1Cl

Intermediate 19

(2,4-Bis-trifluoromethyl-phenyl)-[3-[3-(tert-butyl-dimethyl-silanyloxy)-propyl]-6-methyl-4-(3-thiazol-2-yl-pyrazol-1-yl)-pyridin-2-yl]-amine To a vial containing Pd(dba)$_3$ (17 mg, 0.1 eq), 2-(Dicyclohexylphosphino)-2'-methylbiphenyl (20 mg, 0.3 eq) and K$_3$PO$_4$ (103 mg, 2.7 eq), at r.t., under N$_2$, were added a solution of intermediate 18 (80 mg, 0.18 mmol) in anh. DME (0.5 mL) and a solution of 2,4-bis(trifluoromethyl) aniline (82 mg, 2 eq) in dry DME (0.5 mL). The reaction mixture was submitted to microwave irradiation five times (3×10 min+30 min+60 min) with these observed parameters: P=110 W; T=100° C., p=18 psi. The solution was diluted with water and extracted with EtOAc. The combined organic extracts were dried over anhydrous Na$_2$SO$_4$, filtered and concentrated to dryness in vacuo. The crude product was purified by flash chromatography (silica gel, cHex/Et$_2$O 7:3) to give 49 mg of the title compound as a yellow oil.

NMR ($^1$H, CDCl$_3$): δ 8.58 (d, 1H), 7.89 (d, 1H), 7.85 (d, 1H), 7.77 (dd, 1H), 7.76 (d, 1H), 7.34 (d, 1H), 7.23 (bs, 1H), 7.08 (d, 1H), 6.86 (s, 1H), 3.67 (t, 2H), 2.69 (m, 2H), 2.3 (s, 3H), 1.90 (m, 2H), 0.8 (s, 9H), −0.02 (s, 6H). MS (m/z): 642 [M+1]$^+$

Intermediate 20

3-[2-(2,4-Bis-trifloromethyl-phenylamino)-6-methyl-4-(3-thiazol-2-yl-pyrazol-1-yl)-pyridin-3-yl]-propan-1-ol To a solution of intermediate 19 (60 mg, 0.094 mmol) in anh. THF (2 mL) was added TEA.3HF (0.046 mL, 3 eq). The reaction mixture was stirred at room temperature for 12 hr. Then a saturated solution of $NH_4Cl$ was added to the reaction mixture and it was extracted with EtOAc. The combined organic extracts were dried over $Na_2SO_4$, filtered and concentrated in vacuo. The crude product was purified by flash chromatography (silica gel, cHex/EtOAc 1:1) to give 34.6 mg of the title compound as a white solid.

NMR ($^1$H, $CDCl_3$): δ 8.62 (d, 1H), 7.90 (d, 1H), 7.85 (bs, 1H), 7.76 (dd, 1H), 7.7 (d, 1H), 7.37 (bs, 1H), 7.36 (d, 1H), 7.07 (d, 1H), 6.83 (s, 1H), 3.73 (t, 2H), 2.73 (t, 2H), 2.52 (s, 3H), 2.04 (m, 2H). MS (m/z): 528 $[M+1]^+$

Intermediate 21

2,4-Bis-trifluoromethyl-phenyl)-[3-(3-bromo-propyl)-6-methyl-4-(3-thiazol-2-yl-pyrazol-1-yl-pyridin-2-yl]-amine To a solution of intermediate 20 (34.6 mg, 0.066 mmol) in anh. $CH_2Cl_2$ (1 mL) was added $CBr_4$ (44 mg, 2 eq) and $PPh_3$ (34 mg, 2 eq). The reaction mixture was stirred at room temperature for 1 hr. Then a saturated aqueous solution of $NaHCO_3$ was added to the reaction mixture and it was extracted with EtOAc. The combined organic extracts were dried over $Na_2SO_4$, filtered and concentrated in vacuo. The crude product was purified by flash chromatography (silica gel, cHex/EtOAc 7:3) to give 25.7 mg of the title compound as a white solid.

NMR ($^1$H, $CDCl_3$): δ 8.6 (d, 1H), 7.90 (d, 1H), 7.87 (d, 1H), 7.77 (m, 1H), 7.37 (d, 1H), 7.15 (bs, 1H), 7.10 (d, 1H), 6.84 (s, 1H), 3.47 (t, 2H), 2.78 (m, 2H), 2.52 (s, 3H), 2.3 (m, 2H). MS (m/z): 590 $[M]^+$, 1Br; 510 $[M-Br]^+$

Intermediate 22

4-[3-[2-(tert-Butyl-dimethyl-silanyloxy)-ethyl]-6-methyl-4-(3-thiazol-2-yl-pyrazol-1-yl)-pyridin-2-ylamino]-3-methyl-benzonitrile To a solution of intermediate 8 (186 mg, 0.43 mmol) in anh. DME (1 mL) were added $Pd_2(dba)_3$ (39 mg, 0.1 eq), 2-(dicyclohexylphosphino)-2'-methylbiphenyl (47 mg, 0.3 eq), $K_3PO_4$ (246 mg, 2.6 eq) and 3-methyl-4-amino benzonitrile (113 mg, 2 eq) and the reaction mixture was submitted to microwave irradiation (150 W, 100° C., 60 psi) for 20 min. The reaction was then quenched with an aqueous solution of saturated $NH_4Cl$, extracted with EtOAc, washed with brine, dried over anh. $Na_2SO_4$, filtered and concentrated in vacuo. The crude product was purified by flash chromatography (silica gel, cHex/EtOAc 8:2) to give 61 mg of the title compound as a white solid.

NMR ($^1$H, $CDCl_3$): δ 8.30 (d, 1H), 8.06 (bs, 1H), 7.89 (d, 1H), 7.78 (d, 1H), 7.46 (dd, 1H), 7.44 (d, 1H), 7.36 (d, 1H), 7.09 (d, 1H), 6.81 (s, 1H), 4.34 (m, 2H), 2.82 (t, 2H), 2.56 (s, 3H), 2.36 (s, 3H), 0.85 (s, 9H), 0.02 (s, 6H). MS (m/z): 531 $[MH]^+$.

Intermediate 23

4-[3-(2-Hydroxy-ethyl)-6-methyl-4-(3-thiazol-2-yl-pyrazol-1-yl)-pyridin-2-ylamino]-3-methyl-benzonitrile To a solution of intermediate 22 (61 mg, 0.115 mmol) in anh. THF (2 mL) was added $Et_3N.3HF$ (0.056 ml, 3 eq) and the reaction mixture was stirred for 15 hr at room temperature. The reaction was then quenched with an aqueous solution of saturated $NH_4Cl$, extracted with EtOAc, washed with brine, dried over anh. $Na_2SO_4$, filtered and concentrated in vacuo. The product was purified by flash chromatography (silica gel, cHex/EtOAc 1:1) to give 46 mg of the title compound as a white solid.

NMR ($^1$H, $CDCl_3$): δ 8.39 (bs, 1H), 8.14 (d, 1H), 7.90 (d, 1H), 7.79 (d, 1H), 7.46 (m, 2H), 7.36 (d, 1H), 7.09 (d, 1H), 6.82 (s, 1H), 4.34 (m, 2H), 2.83 (t, 2H), 2.54 (s, 3H), 2.34 (s, 3H). MS (m/z): 417 $[MH]^+$.

Intermediate 24

4-[3-(2-Hydroxy-ethyl)-6-methyl-4-(3-thiazol-2-yl-pyrazol-1-yl)-pyridin-2-ylamino]-3-trifluoromethyl-benzonitrile To a solution of intermediate 8 (106 mg, 0.244 mmol) in anh. DME (1 mL) were added $Pd_2(dba)_3$ (22 mg, 0.1 eq), 2-(dicyclohexylphosphino)-2'-methylbiphenyl (27 mg, 0.3 eq), $K_3PO_4$ (140 mg, 2.7 eq) and 3-trifluoromethyl-4-amino benzonitrile (91 mg, 2 eq) and the reaction mixture was submitted to microwave irradiation (150 W, 100° C., 60 psi) for 20 min. The reaction was then quenched with an aqueous solution of saturated $NH_4Cl$, extracted with EtOAc, washed with brine, dried over anh. $Na_2SO_4$, filtered and concentrated in vacuo. The product was purified by flash chromatography (silica gel, cHex/EtOAc 8:2) and the isolated product containing some unreacted aniline was used in the next step without further purification.

To a solution of the mixture obtained above (120 mg) in anh. THF (5 mL) was added $Et_3N.3HF$ (0.063 ml, 3 eq) and the reaction was stirred for 15 hr at room temperature. The reaction was then quenched with an aqueous solution of saturated $NH_4Cl$, extracted with EtOAc, washed with brine, dried over anh. $Na_2SO_4$, filtered and concentrated in vacuo. The product was purified by flash chromatography (silica gel, cHex/EtOAc 1:1). to give 40 mg of the title compound as a white solid.

NMR ($^1$H, $CDCl_3$): δ 8.81 (bs, 1H), 8.22 (d, 1H), 7.90 (d, 1H), 7.87 (d, 1H), 7.79 (d, 1H), 7.68 (dd, 1H), 7.37 (d, 1H), 7.17 (d, 1H), 6.92 (s, 1H), 4.26 (q, 2H), 2.87 (t, 2H), 2.54 (s, 3H), 2.63 (t, 1H). MS (m/z): 471 $[MH]^+$.

Intermediate 25

[3-[2-(tert-Butyl-dimethyl-silanyloxy)-ethyl]-6-methyl-4-(3-thiazol-2-yl-pyrazol-1-yl)-pyridin-2-yl]-(2-methyl-4-trifluoromethoxy-phenyl)-amine To a solution of intermediate 8 (110 mg, 0.253 mmol) in anh. DME (1 mL), at r.t., under $N_2$, were added $Pd_2(dba)_3$ (23 mg, 0.1 eq), 2-(dicyclohexylphosphino)-2'-methylbiphenyl (28 mg, 0.3 eq), $K_3PO_4$ (145 mg, 2.7 eq) and 2-methyl-4-trifluoromethyl aniline (97 mg, 2 eq) and the reaction mixture was submitted to microwave irradiation (150 W, 100° C., 60 psi) for 20 min. The reaction was then quenched with an aqueous solution of saturated $NH_4Cl$, extracted with EtOAc, washed with brine, dried over anh. $Na_2SO_4$, filtered and concentrated in vacuo. The product was purified by flash chromatography (silica gel, cHex/EtOAc 7:3) to give 80 mg of the title compound as a yellow oil.

NMR ($^1$H, CDCl$_3$): δ 8.05 (d, 1H), 7.83 (bs, 1H), 7.78 (d, 1H), 7.7 (d, 1H), 7.46 (dd, 1H), 7.44 (d, 1H), 7.36 (d, 1H), 7.09 (d, 1H), 6.81 (s, 1H), 4.34 (m, 2H), 2.82 (t, 2H), 2.56 (s, 3H), 2.36 (s, 3H), 0.85 (s, 9H), 0.023 (s, 6H). MS (m/z): 590 [MH]$^+$.

Intermediate 26

2-[6-Methyl-2-(2-methyl-4-trifluoromethoxy-phenylamino)-4-(3-thiazol-2-yl-pyrazol-1-yl)-pyridin-3-yl]-ethanol To a solution of intermediate 25 (80 mg, 0.135 mmol) in anh. THF (2 mL) was added Et$_3$N.3HF (66 μL, 8 eq) and the reaction mixture was stirred for 15 hr at room temperature. The reaction was then quenched with an aqueous solution of saturated NH$_4$Cl, extracted with EtOAc, washed with brine, dried over Na$_2$SO$_4$, filtered and concentrated in vacuo. The product was purified by flash chromatography (silica gel, cHex/EtOAc 1:1) to give 48 mg of the title compound as a colorless oil.

NMR ($^1$H, CDCl$_3$): δ 7.91 (bs, 1H), 7.85 (d, 1H), 7.7 (d, 1H), 7.65 (d, 1H), 7.30 (d, 1H), 7.15-6.95 (m, 3H), 6.65 (s, 1H), 4.34 (m, 2H), 2.83 (t, 2H), 2.54 (s, 3H), 2.34 (s, 3H).

Example 1

Synthesis of Representative Compounds of Structure (IIIa)

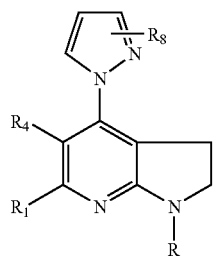

(IIIa)

Example 1-1

1-(2,4-Bis-trifluoromethyl-phenyl)-6-methyl-4-(3-thiazol-2-yl-pyrazol-1-yl)-2,3-dihydro-1H-pyrrolo[2,3-b]pyridine To a solution of intermediate 10 (40 mg, 0.078 mmol) in anh. CH$_2$Cl$_2$ (2 mL), at r.t., under N$_2$, were added CBr$_4$ (52 mg, 2 eq) and PPh$_3$ (41 mg, 2 eq) and the reaction mixture was stirred for 3 hr. The reaction was then quenched with an aqueous solution of saturated NaHCO$_3$, extracted with EtOAc, washed with brine, dried over anh. Na$_2$SO$_4$, filtered and concentrated in vacuo. The product was purified by flash chromatography (silica gel, cHex/EtOAc 2:1) to give 18 mg of the title compound as a white solid.

Alternatively:

Example 1-1

1-(2,4-Bis-trifluoromethyl-phenyl)-6-methyl-4-(3-thiazol-2-yl-pyrazol-1-yl)-2,3-dihydro-1H-pyrrolo[2,3-b]pyridine To a mixture of tris(dibenzylidenacetone)palladium(0) (3.2 mg, 0.1 eq), 2-(dicyclohexylphosphino)-2'-methylbiphenyl (3.8 mg, 0.3 eq) and K$_3$PO$_4$ (20 mg, 2.8 eq) in a crimp cap microwave vial was added a solution of intermediate 14 (10 mg, 0.035 mmol) and 2,4-bis(trifluoromethyl)-bromobenzene (6 μL, 1 eq) in anh. DME (1 mL), under N$_2$. The reaction mixture was submitted to microwave irradiation for two cycles (2×10 min) with these observed parameters: P=150 W; T=100° C., p=60 psi Then water (1 mL) was added and the product was extracted with EtOAc. The combined organic extracts were washed with sat. aq. NaCl (5 mL) and dried over anh. Na$_2$SO$_4$. The solids were filtered and the solvent evaporated to give a crude product, which was purified by flash chromatography (silica gel, cHex/EtOAc 7:3). The title compound was obtained as a colourless oil (1 mg, 0.002 mmol).

Example 1-2

3-Methyl-4-[6-methyl-4-(3-thiazol-2-yl-pyrazol-1-yl)-2,3-dihydro-1H-pyrrolo[2,3-b]pyridin-1-yl]-benzonitrile To a solution of intermediate 23 (44 mg, 0.106 mmol) in anh. CH$_2$Cl$_2$ (2 mL) were added CBr$_4$ (71 mg, 2 eq) and PPh$_3$ (60 mg, 2 eq) and the reaction mixture was stirred for 3 hr at room temperature. The reaction was then quenched with an aqueous solution of saturated NaHCO$_3$, extracted with EtOAc, washed with brine, dried over anh. Na$_2$SO$_4$, filtered and concentrated in vacuo. The product was purified by flash chromatography (silica gel, cHex/EtOAc 4:1) to give 18 mg of the title compound as a white solid.

Example 1-3

4-[6-Methyl-4-(3-thiazol-2-yl-pyrazol-1-yl)-2,3-dihydro-1H-pyrrolo[2,3-b]pyridin-1-yl]-3-trifluoromethyl-benzonitrile To a solution of intermediate 24 (40 mg, 0.085 mmol) in anh. CH$_2$Cl$_2$ (2 mL) were added CBr$_4$ (56 mg, 2 eq) and PPh$_3$ (45 mg, 2 eq) and the reaction mixture was stirred for 3 hr at room temperature. The reaction was then quenched with an aqueous solution of saturated NaHCO$_3$, extracted with EtOAc, washed with brine, dried over anh. Na$_2$SO$_4$, filtered and concentrated in vacuo. The product was purified by flash chromatography (silica gel, cHex/EtOAc 2:1) to give 13 mg of the title compound as a white solid.

Example 1-4

6-Methyl-1-(2-methyl-trifluoromethoxy-phenyl)-4-(3-thiazol-2-yl-pyrazol-1-yl)-2,3-dihydro-1H-pyrrolo[2,3-b]pyridine To a solution of intermediate 26 (48 mg, 0.101 mmol) in anh. CH$_2$Cl$_2$ (2 mL) were added CBr$_4$ (66 mg, 2 eq) and PPh$_3$ (53 mg, 2 eq) and the reaction mixture was stirred for 3 hr at room temperature. The reaction was then quenched with an aqueous solution of saturated NaHCO$_3$, extracted with EtOAc, washed with brine, dried over anh. Na$_2$SO$_4$, filtered and concentrated in vacuo. The product was purified by flash chromatography (silica gel, cHex/EtOAc 8:2) to give 10 mg of the title compound as a white solid.

Example 1-5

1-(4-Methoxy-2-methyl-phenyl)-6-methyl-4-(3-thiazol-2-yl-pyrazol-1-yl)-2,3-dihydro-1H-pyrrolo[2,3-b]pyridine To a solution of intermediate 28 (31 mg, 0.075 mmol, 1 eq.) in DCM dry (5 ml), was added $CBr_4$ (53 mg, 0.16 mmol, 2.1 eq.) and triphenylphosphine (42 mg, 0.16 mmol, 2.1 eq.) under $N_2$. The reaction mixture was stirred at RT for 15 hrs. Then water (10 ml) was added and the aqueous phase was extracted with EtOAc (20 ml). The organic layer was dried over $Na_2SO_4$, filtered and concentrated in vacuo. The crude was purified by flash chromatography (Eluents:cyclohexane/ethyl acetate 7:3) to give 5.2 mg of VSAF/6274/4/1 as a colorless oil.

Example 1-6

1-(2,4-Bis-trifluoromethyl-phenyl)-6-methyl-4-(3-morpholin-4-yl-pyrazol-1-yl)-2,3-dihydro-1H-pyrrolo[2,3-b]pyridine Prepared analogously to example 1-1 using 4-(1H-pyrazol-3-yl)-morpholine (*J. Org. Chem.*, 1984, 269-276) instead of 2-(1H-pyrazol-3-yl)-thiazole in the preparation of intermediate 2.

Example 1-7

1-(2,4-Bis-trifluoromethyl-phenyl)-6-methyl-4-(3-pyridin-2-yl-pyrazol-1-yl)-2,3-dihydro-1H-pyrrolo[2,3-b]pyridine Prepared analogously to example 1-1 using 2-(1H-Pyrazol-3-yl)-pyridine (commercially available) instead of 2-(1H-pyrazol-3-yl)-thiazole in the preparation of intermediate 2.

Example 1-8

4-[1,3']Bipyrazolyl-1'-yl-1-(2,4-bis-trifluoromethyl-phenyl)-6-methyl-2,3-dihydro-1H-pyrrolo[2,3-b]pyridine Prepared analogously to example 1-1 using 1'H-[1,3'] bipyrazolyl (from 1H-pyrazol-3-ylamine: *J. Heterocycl. Chem.*, 1983, 1629-1639; then *J. Heteroycl. Chem.*, 1989, 733-738) instead of 2-(1H-pyrazol-3-yl)-thiazole in the preparation of intermediate 2.

All the analytical data are set forth in the following Table 1-1.

TABLE 1-1

(IIIa)

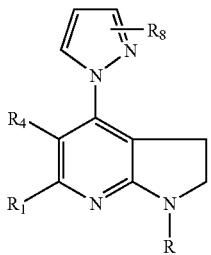

| Cpd. No. | R | $R_1$ | $R_2$—$R_3$— | Analytical Data |
|---|---|---|---|---|
| 1-1 | 2,4-bistrifluoro-methylphenyl | $CH_3$ | | NMR ($^1$H, DMSO): δ 8.64 (d, 1H), 8.17 (dd, 1H), 8.13 (d, 1H), 7.94 (d, 1H), 7.84 (d, 1H), 7.80 (d, 1H), 7.09 (m, 2H), 3.97 (t, 2H), 3.56 (t, 2H), 2.24 (s, 3H). MS (m/z): 496 [MH]$^+$. |
| 1-2 | 2-methyl-4-cyano | $CH_3$ | | NMR ($^1$H, DMSO): δ 8.02 (d, 1H), 7.90 (d, 1H), 7.59 (d, 1H), 7.53 (dd, 1H), 7.41 (d, 1H), 7.38 (d, 1H), 6.76 (s, 1H), 4.04 (t, 2H), 3.62 (t, 2H), 2.41 (s, 3H), 2.33 (s, 3H). MS (m/z): 399 [MH]$^+$. |

TABLE 1-1-continued (IIIa)

[Structure showing pyrrolo-pyridine core with R, R1, R4, R8 substituents and pyrazole]

| Cpd. No. | R | R1 | R2—R3— | Analytical Data |
|---|---|---|---|---|
| 1-3 | 2-trifluoromethyl-4-cyano | CH3 | [thiazolyl-pyrazolyl group] | NMR ($^1$H, CDCl$_3$): δ 8.00 (m, 2H), 7.9–7.8 (d + d, 2H), 7.65 (d, 1H), 7.35 (d, 1H), 7.10 (d, 1H), 6.80 (s, 1H), 4.00 (t, 2H), 3.60 (t, 2H), 3.56 (t, 2H), 2.40 (s, 3H). MS (m/z): 453 [MH]$^+$. |
| 1-4 | 2-methyl-4-trifluoromethoxy | CH3 | [thiazolyl-pyrazolyl group] | NMR ($^1$H, DMSO): δ 8.01 (d, 1H), 7.89 (d, 1H), 7.5 (d, 1H), 7.45 (dd, 1H), 7.20 (d, 1H), 7.1 (dd, 2H), 6.65 (s, 1H), 3.9 (t, 2H), 3.56 (t, 2H), 2.32 (s, 3H), 2.25 (s, 3H). MS (m/z): 458.5 [MH]$^+$. |
| 1-5 | 2-methyl-4-methoxy | CH3 | [thiazolyl-pyrazolyl group] | NMR ($^1$H, CDCl$_3$): δ 7.97 (d, 1H), 7.86 (d, 1H), 7.33 (d, 1H), 7.17 (d, 1H), 7.10 (d, 1H), 6.78 (m, 2H), 6.61 (s, 1H), 3.90 (t, 2H), 3.80 (s, 3H), 3.52 (t, 2H), 2.34 (s, 3H), 2.23 (s, 3H). MS (m/z): 404 [M + 1]$^+$ |

Example 2

Synthesis of Representative Compounds of Structure (IIIb)

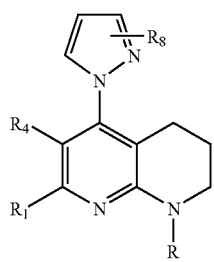

(IIIb)

All the analytical data are set forth in the following Table 2-1.

Example 2-1

1-(2,4-Bis-trifluoromethyl-phenyl)-7-methyl-5-(3-thiazol-2-yl-pyrazol-1-yl)-1,2,3,4-tetrahydro-[1,8]naphthyridine To a solution of intermediate 21 (24.8 mg, 0.042 mmol) in anh. N-metylpyrrolidinone (2 mL) was added Et$_3$N (12 μL, 2 eq) under N$_2$. The reaction mixture was submitted to microwave irradiation for 10 min with these observed parameters: P=90 W; T=99° C., p=6 psi. Then a saturated aqueous solution of NH$_4$Cl was added to the reaction mixture and the aqueous phase was extracted with EtOAc. The combined organic extracts were washed with a saturated solution of NH$_4$Cl (3×), dried over Na$_2$SO$_4$, filtered and concentrated in vacuo. The crude product was purified by SCX Column (Eluents: CH$_2$Cl$_2$, MeOH and a solution of conc. NH$_4$OH in MeOH (25%) to elute the desired product) to give 18.4 mg of the title compound as a white foam.

TABLE 2-1

| Cpd. No. | R | $R_1$ | $R_2$—$R_3$— | Analytical Data |
|---|---|---|---|---|
| 2-1 | 2,4-bistrifluoro-methylphenyl | $CH_3$ | 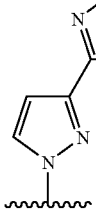 | NMR ($^1$H, CDCl$_3$): δ 8.02 (bs, 1H), 7.89 (d, 1H), 7.88 (dd, 1H), 7.74 (d, 1H), 7.46 (d, 1H), 7.35 (d, 1H), 7.06 (d, 1H), 6.59 (s, 1H), 3.66 (bm, 2H), 2.97 (bm, 1H), 2.85 (bm, 1H), 2.18 (s, 3H), 2.09 (bm, 1H), 2.04 (bm, 1H). MS (m/z): 510 [M + 1]$^+$ |

Example 3

CRF Binding Activity

CRF binding affinity has been determined in vitro by the compounds' ability to displace $^{125}$I-oCRF and $^{125}$I-Sauvagine for CRF1 and CRF2 SPA, respectively, from recombinant human CRF receptors expressed in Chinese Hamster Ovary (CHO) cell membranes. For membrane preparation, CHO cells from confluent T-flasks were collected in SPA buffer (HEPES/KOH 50 mM, EDTA 2 mM; MgCl$_2$ 10 mM, pH 7.4.) in 50 mL centrifuge tubes, homogenized with a Polytron and centrifuged (50,000 g for 5 min at 4° C.: Beckman centrifuge with JA20 rotor). The pellet was resuspended, homogenized and centrifuged as before.

The SPA experiment has been carried out in Optiplate by the addition of 100 µL the reagent mixture to 1 µL of compound dilution (100% DMSO solution) per well. The assay mixture was prepared by mixing SPA buffer, WGA SPA beads (2.5 mg/mL), BSA (1 mg/mL) and membranes (50 and 5 µg of protein/mL for CRF1 and CRF2 respectively) and 50 pM of radioligand.

The plate was incubated overnight (>18 hrs) at room temperature and read with the Packard Topcount with a WGA-SPA $^{125}$I counting protocol.

Example 4

CRF Functional Assay

Compounds of the invention were characterised in a functional assay for the determination of their inhibitory effect. Human CRF—CHO cells were stimulated with CRF and the receptor activation was evaluated by measuring the accumulation of cAMP.

CHO cells from a confluent T-flask were resuspended with culture medium without G418 and dispensed in a 96-well plate, 25,000 c/well, 100 µL/well and incubated overnight. After the incubation the medium was replaced with 100 µL of cAMP IBMX buffer warmed at 37° C. (5 mM KCl, 5 mM NaHCO$_3$, 154 mM NaCl, 5 mM HEPES, 2.3 mM CaCl$_2$, 1 mM MgCl$_2$; 1 g/L glucose, pH 7.4 additioned by 1 mg/mL BSA and 1 mM IBMX) and 1 µL of antagonist dilution in neat DMSO. After 10 additional minutes of incubation at 37° C. in a plate incubator without CO2, 1 µL of agonist dilution in neat DMSO was added. As before, the plate was incubated for 10 minutes and then cAMP cellular content was measured by using the Amersham RPA 538 kit.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound which is 1-(4-methoxy-2-methyl-phenyl)-6-methyl-4-(3-thiazol-2-yl-pyrazol-1-yl)-2,3-dihydro-1H-pyrrolo[2,3-b]pyridine or a pharmaceutically acceptable salt thereof.

* * * * *